United States Patent

Junien et al.

[11] Patent Number: 5,965,701
[45] Date of Patent: Oct. 12, 1999

[54] KAPPA RECEPTOR OPIOID PEPTIDES

[75] Inventors: Jean Louis Junien, Sevres, France; Pierre J.M. Riviére, San Diego, Calif.; Claudio D. Schteingart, La Jolla, Calif.; Javier Sueiras Diaz, La Jolla, Calif.; Jerzy A. Trojnar, Solana Beach, Calif.; Todd W. Vanderah, Tucson, Ariz.

[73] Assignee: Ferring BV, Netherlands

[21] Appl. No.: 08/997,208

[22] Filed: Dec. 23, 1997

[51] Int. Cl.$^6$ ...................................................... C07K 5/00
[52] U.S. Cl. ................... 530/330; 514/2; 514/18
[58] Field of Search ........................ 530/330; 514/2, 514/18

[56] References Cited

U.S. PATENT DOCUMENTS

| | | | |
|---|---|---|---|
| 5,367,053 | 11/1994 | Dooley et al. | 530/329 |
| 5,610,271 | 3/1997 | Dooley et al. | 530/328 |

OTHER PUBLICATIONS

Riviere et al., *Gastroenterology*, 104:724–731 (1993).
Diop et al., *Eur. J. Pharm.*, 271:65–71 (1994).
Junien and Riviere, *Alimentary Pharmacology and Therapeutics*, 9:117–126 (1995).
Vonvoigtlander, P.F. et al., *J. Pharm. Exper. Therapeutics*, 224:7–12 (1983).
G. A. Bentley et al., *Br. J. Pharmac.*, 73:325–332 (1981).
Vanderah, T.W. et al., *J. Pharm. Exper. Therapeutics*, 262:190–197 (1992).

Primary Examiner—Cecilia J. Tsang
Assistant Examiner—C. Delacroix Muirheid
Attorney, Agent, or Firm—Fitch, Even, Tabin & Flannery

[57] ABSTRACT

Peptides which exhibit high selectivity for the kappa opioid receptor (KOR) and long duration of peripheral action without significant entry into the brain are created which are sequences of four D-isomer amino acid residues having a C-terminus which is a mono or di-substituted amide. Representative compounds, which have an affinity for the KOR at least 1,000 times their affinity for the mu opioid receptor and an $ED_{50}$ of not greater than about 0.5 mg/kg, include H-D-Phe-D-Phe-D-Nle-D-Arg-NHEt, H-D-Phe-D-Phe-D-Nle-D-Arg-morpholinyl, H-D-Phe-D-Phe-D-Nle-D-Arg-NH-4-picolyl, H-D-Phe-D-Phe-D-Nle-D-Arg-NHPr, H-D-Phe-D-Phe-D-Nle-D-Arg-thiomorpholinyl, H-D-Phe-D-Phe-D-Nle-D-Arg-NEt$_2$, H-D-Phe-D-Phe-D-Nle-D-Arg-NHMe, H-D-Phe-D-Phe-D-Leu-D-Orn-morpholinyl, H-D-Phe-D-Phe-D-Nle-D-Arg-NHhEt, H-D-Phe-D-Phe-D-Nle-D-Arg-NH-cyclopropyl, H-D-Ala(2Thi)-D-4Cpa-D-Leu-D-Arg-morpholinyl, H-D-Phe-D-Phe-D-Nle-D-Arg-piperidinyl, H-D-Phe-D-Phe-D-Leu-D-Orn-NHEt, H-D-Phe-D-Phe-D-Leu-D-Lys-morpholinyl, and H-D-Phe-D-Phe-D-Nle-D-Arg-piperazinyl.

21 Claims, No Drawings

KAPPA RECEPTOR OPIOID PEPTIDES

The present invention relates generally to synthetic opioid peptides, particularly to opioid peptides which are highly selective kappa receptor agonists and more particularly to such agonists that (a) do not penetrate into the brain and (b) exhibit a long-lasting antinociceptive activity in vivo.

BACKGROUND OF THE INVENTION

Kappa opioid receptors (KORs) are present in the brain, spinal cord, and on the central and peripheral terminals and cell bodies of the primary sensory afferents (somatic and visceral), as well as on immune cells.

KORs which are located in the brain have been shown to mediate the central analgesic effects of molecules, commonly referred to as kappa agonists, which activate such KORs. This finding led to numerous attempts (i.e. Spiradoline from Upjohn and Enadoline from Parke-Davis) to develop brain-penetrating, non-peptidic kappa agonists for use as original analgesics which would be devoid of the unwanted side effects (constipation, respiratory depression, dependence and addiction) of morphinic analogs that act on mu opioid receptors (MORs). The analgesic activity, as well as the lack of mu-opioid side effects, of this class of compounds has been established both in animals and humans. However, some systemic kappa agonists were also shown to induce specific side effects such as diuresis, sedation and dysphoria, mediated through kappa receptors located in the brain, which resulted in the discontinuation of their development.

In addition to such centrally mediated analgesia, stimulation of KORs located either in the periphery or in the spinal cord may also produce analgesia. However, neither peripheral nor spinal KORs were associated with any of the side effects of systemic kappa agonists. Therefore, as long as it is possible to create kappa receptor opioid agonists that do not enter the brain (following either peripheral or spinal administration), it should be possible to obtain safe and original analgesics.

It is now considered that peptidic opioid agonists that are selective for the KOR should be ideal for this purpose because they are likely, at the most, to only poorly enter the brain after either peripheral or spinal administration; therefore, they are expected to be devoid of central side effects. Parenteral (i.v., i.m., s.c. epidural, topical or local) routes of administration may thus be suitable for this class of compounds to treat pain in conditions associated with inflammation, such as rheumatoid arthritis, or post-operative pain, such as that resulting from eye surgery, dental surgery, articulation surgery, abdominal surgery, childbirth and cesarian section. Furthermore, alleviation of abdominal postsurgery symptoms (digestive ileus) is presently considered to be a major therapeutic target of peptidic kappa agonists. These symptoms include motility disorders such as bloating, nausea, and intestinal transit inhibitions associated with sensitivity disorders, such as pain possibly induced by distension. Such motor disturbances are considered to be the consequence of a prior alteration of visceral sensitivity resulting from nerve sensitization by local inflammatory process, and it has been shown in animal models that compounds which block pain may also reverse motor impairments (Riviere et al., Gastroenterology, 104:724–731, 1993). Indeed, non-peptidic kappa agonists were shown to produce antinociception in experimental ileus that was associated with a restoration of normal motor functions. Such provides a rationale for developing nonbrain-penetrating kappa agonists for treatment of post-operative pain and digestive ileus (Friese et al., Life Sciences, 60(9):625–634, 1997). Because such kappa agonists generally do not exhibit a constipating or antitransit side effect, they have a major advantage for this indication compared to morphine-like compounds.

It has also been shown that kappa agonists produce peripheral antinociception in models of intestinal as well as colonic hyperalgesia induced by mild and local inflammation (Diop et al., Eur. J. Pharm., 271:65–71, 1994). As a result, Irritable Bowel Syndrome (IBS), which includes exaggerated visceral pain due to a visceral hypersensitivity possibly linked to a local inflammation, is also a target for a peripheral kappa agonist (Junien and Riviere, Alimentary Pharmacology and Therapeutics, 9:117–126, 1995).

In addition to the gastrointestinal tract, other viscera showing a pathological condition that involves activation and/or sensitization (i.e. local inflammation) of primary sensory afferents are also considered to represent appropriate targets for such a kappa receptor opioid. Examples of these conditions where kappa receptor opioids can be used include urinary incontinence due to bladder inflammation (cystitis), dysmennorhea, vasomotor rhinitis, ocular inflammation, and kidney or bladder stone-induced pain.

It was established in somatic tissues that kappa agonists also block neurogenic inflammation by inhibiting the release of substance P from primary sensory afferents. Assuming such activity is also present in GI and visceral tissues, peripheral kappa agonists would be expected to have an ameliorating effect in conditions where pain or visceral hypersensitivity is associated with neurogenic inflammation (e.g. bladder cystitis).

Kappa opioid agonists are also known to act on the immune system and have primarily an inhibitory role on immune cells. Their effects include (i) suppression of T cell-dependent antibody production, (ii) alteration of mitogen- and antigen-induced lymphocyte proliferation, (iii) modulation of natural killer (NK) cell- and T cell-mediated cytotoxicity; (iv) chemotaxis of peripheral blood derived mononuclear cells (PBMC), and (v) alteration of PMBC function. These effects might be of interest in some specific indications, where it is important to lower the immune response.

Peptides which will not enter the brain, which exhibit high affinity for the KOR versus the MOR, which have high potency and efficacy, and which exhibit long duration of action in vivo are particularly desired. U.S. Pat. No. 5,610, 271 discloses tetrapeptides containing four D-isomer amino acid residues that bind to KORs but do not exhibit all of these desirable characteristics.

SUMMARY OF THE INVENTION

A genus of peptides has been discovered which exhibit high selectivity for the KOR and long duration of in vivo action and which do not exhibit any significant brain penetration. These peptides comprise a sequence of four D-isomer amino acids having a C-terminus that is either a mono or disubstituted amide. These compounds have the following general formula:

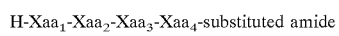

H-Xaa$_1$-Xaa$_2$-Xaa$_3$-Xaa$_4$-substituted amide wherein Xaa$_1$ is (A)D-Phe, (C$^\alpha$Me)D-Phe, D-Tyr, D-Tic or D-Ala(cyclopentyl or thienyl), with A being H, NO$_2$, F, Cl or CH$_3$; Xaa$_2$ is (A')D-Phe, D-1Nal, D-2Nal, D-Tyr or D-Trp, with A' being A or 3,4Cl$_2$; Xaa$_3$ is D-Nle, (B)D-Leu, D-Hle, D-Met, D-Val, D-Phe or D-Ala(cyclopentyl) with B being H or C$^\alpha$Me; Xaa$_4$ is D-Arg, D-Har, D-nArg, D-Lys, D-Lys(Ipr), D-Arg(Et$_2$), D-Har(Et$_2$), D-Amf(G), D-Dbu, (B)D-Orn or D-Orn(Ipr), and with G being H or amidino. Preferred amides include ethylamide, morpholinylamide, 4-picolylamide, piperazineamide, propylamide, cyclopropylamide and diethylamide.

BRIEF DESCRIPTION OF THE PREFERRED EMBODIMENT

The nomenclature used to define the peptides is that specified by Schroder & Lubke, *The Peptides*, Academic Press, 1965, wherein, in accordance with conventional representation, the N-terminus appears to the left and the C-terminus to the right. Where an amino acid residue has isomeric forms, it is the L-isomer form of the amino acid that is being represented herein unless otherwise expressly indicated.

As indicated above, the invention provides peptides which are selective for the KOR and not only exhibit a strong affinity for the KOR but exhibit long duration of in vivo bioactivity. These kappa selective opioid peptides have at least 1,000 times greater binding affinity for the KOR than the MOR, with many compounds having at least 10,000 times greater affinity, and with some compounds exhibiting an affinity of 20,000 or more times greater. However, for many indications it is important that, along with such high selectivity, the kappa agonists should exhibit both a lack of significant brain penetration and a prolonged duration of in vivo antinociceptive activity. Therefore, in addition to the above-mentioned selectivity, preferred compounds exhibit no significant brain penetration while preserving substantial activity for at least about one hour, with the more preferred compounds remaining significantly active for at least about 2 hours, and with the most preferred compounds exhibiting such significant activity for three hours or longer.

As generally indicated hereinbefore, the invention provides a genus of D-isomer tetrapeptides having the formula which follows:

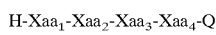

H-Xaa$_1$-Xaa$_2$-Xaa$_3$-Xaa$_4$-Q wherein Xaa$_1$ is (A)D-Phe, (C$^\alpha$Me)D-Phe, D-Tyr, D-Tic or D-Ala(cyclopentyl or thienyl), with A being H, No$_2$, F, Cl or CH$_3$; Xaa$_2$ is (A')D-Phe, D-1Nal, D-2Nal, D-Tyr or D-Trp, with A' being A or 3,4Cl$_2$; Xaa$_3$ is D-Nle, (B)D-Leu, D-Hle, D-Met, D-Val, D-Phe or D-Ala(cyclopentyl) with B being H or C$^\alpha$Me; Xaa$_4$ is D-Arg, D-Har, D-nArg, D-Lys, D-Lys (Ipr), D-Arg(Et$_2$), D-Har(Et$_2$), D-Amf(G), D-Dbu, (B)D-Orn or D-Orn(Ipr), with G being H or amidino; and Q is NR$_1$R$_2$, morpholinyl, thiomorpholinyl, (C)piperidinyl, piperazinyl, mono- or di-substituted piperazinyl or δ-ornithinyl, with R$_1$ being lower alkyl, substituted lower alkyl, benzyl, substituted benzyl, aminocyclohexyl, 2-thiazolyl, 2-picolyl, 3-picolyl or 4-picolyl, R$_2$ being H or lower alkyl; and C being H, 4-hydroxy or 4-oxo.

By D-Nle is meant D-norleucine, and D-Hle represents D-homoleucine. D-Har represents D-homoarginine, and D-nArg represents D-norarginine which is one carbon shorter than D-Arg. By D-Nal is meant the D-isomer of alanine which is substituted by naphthyl on the β-carbon. Preferably, D-2Nal is employed, i.e. the attachment to naphthalene is at the 2-position on the ring structure; however, D-1Nal may also be used. The abbreviations D-Cpa and D-Fpa are used to represent, respectively, chloro-D-Phe and fluoro-D-Phe, with D-4Cpa, D-2Fpa, D-3Fpa and D-4Fpa being preferred. D-Npa means nitro-D-Phe, and D-Mpa is used to represent methyl D-Phe. D-3,4Cpa means 3,4-dichloro-D-Phe. D-Acp represents D-Ala(cyclopentyl). D-Orn represents D-ornithine, and D-Dbu represents alpha, gamma-diamino butyric acid. CML represents C$^\alpha$methyl Leu, and CMP and CMO represent C$^\alpha$Me Phe and C$^\alpha$Me Orn. By D-4Amf is meant D-4(NH$_2$CH$_2$)Phe, and by D-Gmf is meant Amf(amidino) which represents D-Phe where the 4-position is substituted with CH$_2$NHC(NH)NH$_2$. Amd represents amidino, and the symbol D-Amf(Amd) is also used. By D-Tic is meant D-1,2,3,4-tetrahydroisoquinoline-3-carboxylic acid. In Ala(Thi), Thi represents the thienyl group, which is preferably linked at its 2-position to alanine, although 3-thienyl is an equivalent. By Ily and Ior are respectively meant isopropyl Lys and isopropyl Orn where the side chain amino group is alkylated with isopropyl.

By lower alkyl is meant C$_1$ to C$_6$, and preferably C$_1$–C$_4$ but including cyclopropyl and cyclobutyl. Me, Et, Pr, Ipr, Bu, Pn and Bzl are used to represent methyl, ethyl, propyl, isopropyl, butyl, pentyl and benzyl. By Cyp is meant cyclopropyl, and by Cyb is meant cyclobutyl. Although the linkage is preferably to one end of an alkyl chain, the linkage may be elsewhere in the chain, e.g. 3-pentyl which may also be referred to as ethylpropyl. 4Nbz and 4Abz represent 4-nitrobenzyl and 4-aminobenzyl. By 2-, 3- and 4-picolyl (Pic) are meant methylpyridine groups with the attachment being via a methylene in the 2-, 3- or 4-position. By Mor is meant morpholinyl, i.e.

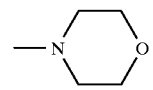

and by Tmo is meant thiomorpholinyl,

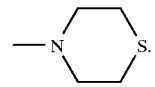

4Ahx is used to represent 4-aminocyclohexyl, and hEt is used to represent hydroxyethyl, i.e. —CH$_2$CH$_2$OH. Aeb is used to represent 4-(2-amino-2-carboxyethyl)benzyl, i.e.

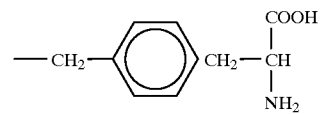

By Pip is meant piperidinyl, and by 4-HyP and OxP are meant 4-hydroxypiperidinyl and 4-oxo-piperidinyl. By Ppz is meant piperazinyl. Ecp represents 4-ethylcarbamoylpiperazinyl; quaternary ammonium moieties, such as 4-dimethyl piperazinyl (Dmp) or other di-lower alkyl substitutions, may also be used. Substituted benzyl is preferably 4-aminobenzyl, i.e.

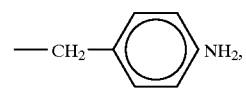

and by 2-Tzl is meant 2-thiazolyl, i.e.

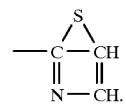

By Dor is meant δ-ornithinyl where the side chain amino group of L-ornithine is connected by an amide bond to the C-terminus.

D-Phe or substituted D-Phe is preferred in the 1-position. The phenyl ring may be substituted at the 2-, 3- and/or 4-positions, and commonly substitutions by chlorine or fluorine at the 2 or 4-position are preferred. The α-carbon atom may also be methylated. Other equivalent residues which resemble D-Phe may also be used, and these include D-Ala(cyclopentyl), D-Ala(thienyl), D-Tyr and D-Tic. The 2-position residue is also preferably D-Phe or substituted D-Phe with such substitutions preferably including a substituent on the 4-position carbon of the phenyl ring or the 3- and 4-positions. Alternatively, D-alanine substituted by naphthyl can be used, as well as D-Trp and D-Tyr. The 3-position is preferably occupied by a residue such as D-Nle, D-Leu, D-CML, D-Hle, D-Met or D-Val; however, D-Ala (cyclopentyl) or D-Phe may also be used. D-Arg and D-Har, which may be substituted with diethyl, are generally preferred for the 4-position; however, D-nArg and other equivalent residues may be used, such as D-Lys or D-Orn (either of which can have its omega-amino group alkylated as by isopropyl or have its α-carbon group methylated). Moreover, D-Dbu, D-4Amf (which is preferably substituted with amidino), and D-His may also be used.

Although it might be expected that good duration of biological action would accrue from the employment of a sequence of 4 D-isomer amino acids, it was surprising to find that the duration of action was generally quite short for the unsubstituted amide and that a long duration of action was obtained only through the incorporation of a substituted amide at the C-terminus. Single substitutions may be in the form of ethyl, methyl, propyl, cyclopropyl and picolyl, as well as other equivalent residues, such as hydroxyethyl, thiazolyl, aminocyclohexyl, benzyl, and substituted benzyl. Generally, lower alkyl or lower cycloalkyl or picolyl substitutents are preferred for single substituted amides. Instead of a single substituted amide, a dialkyl substitution, e.g. diethylamino, is an alternative; however, preferably such a disubstituted C-terminus is occupied by a morpholinyl, thiomorpholinyl or piperidinyl moiety, with the latter being unsubstituted or substituted by 4-hydroxy or 4-oxo. A 4-piperazinyl or substituted 4-piperazinyl moiety may also be used, as can δ-ornithinyl.

It is found that binding is generally an attribute of the amino acid sequence of the tetrapeptide, and preferably the selective kappa receptor opioid peptides should exhibit a binding affinity to the kappa receptor such that its $K_i$ is equal to about 2 nM or less. The long duration of action, which is believed to be primarily an attribute of the structure of the amide attached to the C-terminus, can be effectively tested by the antinociceptive assay described hereinafter, and the most preferred peptides exhibit substantial biological activity for two or three hours and have no significant effect upon the brain.

A preferred subgenus of these opioid peptides has the formula:

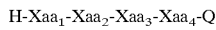

wherein $Xaa_1$ is D-Phe (unsubstituted or substituted by $C^{\alpha}Me$, 2F, 4F or 4Cl) or D-Ala(cyclopentyl or thienyl); $Xaa_2$ is (A')D-Phe, D-1Nal, D-2Nal or D-Trp, with A' being H, 4F, 4Cl, 4NO$_2$ or 3,4Cl$_2$; $Xaa_3$ is D-Nle, D-Leu, D-CML, D-Met or D-Acp; $Xaa_4$ is D-Arg, D-Arg(Et$_2$), D-Lys, D-Ily, D-Har, D-Har(Et$_2$), D-nArg, D-Orn, D-Ior, D-Dbu, D-Amf, and D-Amf(Amd); and Q is NR$_1$R$_2$, Mor, Tmo, Pip, 4-HyP, OxP or Ppz, with R$_1$ being Me, Et, Pr, Bu, hEt, Cyp, Bzl or 4-picolyl, and R$_2$ being H or Et.

An additional preferred subgenus of kappa opioid peptides has the formula:

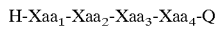

wherein $Xaa_1$ is D-Phe, D-4Fpa, D-2Fpa, D-4Cpa, D-Acp or D-Ala(Thi); $Xaa_2$ is D-Phe, D-4Fpa, D-4Cpa, D1Nal, D-2Nal or D-Trp; $Xaa_3$ is D-Nle, D-Met, D-CML or D-Leu; $Xaa_4$ is D-Arg, D-Lys, D-Har, D-nArg or D-Orn; and Q is NR$_1$R$_2$, Mor, Tmo, Pip, 4-HyP or Ppz, with R$_1$ being Et, Pr, Bu, Cyp, hEt, Bzl or 4-Pic, and R$_2$ being H or Et.

A further preferred subgenus of kappa opioid peptides has the formula:

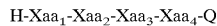

wherein $Xaa_1$ is D-Phe, D-4Fpa, D-2Fpa, D-Acp or D-Ala (2Thi); $Xaa_2$ is (A)D-Phe, D-1Nal, D-2Nal or D-Trp, with A being 4F or 4Cl; $Xaa_3$ is D-Nle, D-Met or D-Leu; $Xaa_4$ is D-Arg, D-Har, D-nArg, D-Lys, D-Orn or D-Amf(Amd); and Q is NHR$_1$, Mor, Tmo, Pip or Ppz, with R$_1$ being Et, Pr or 4Pic.

The foregoing genus and subgenuses of opioid peptides have been found to have extended duration of antinociceptive in vivo activity as a result of incorporating a substituted amide at the C-terminus of the position-4 amino acid residue. This particular unexpected attribute renders such peptides particularly valuable as certain of them remain active in vivo for periods of three hours and longer. Certain tetrapeptides having the aforementioned sequence but having a simple C-terminal amide also demonstrate high selectivity for the KOR, as compared to the MOR; however, they generally exhibit only short term duration of action. It is fully expected that such opioid peptides will exhibit extended term of duration when synthesized so as to have a substituted amide, such as morpholinylamide, at the C-terminus. It has consistently been found that, when a tetrapeptide showing high and selective binding to KOR is synthesized with a substituted amide at the C-terminus, for example, ethylamide or morpholinylamide, such corresponding tetrapeptide exhibits extended duration of antinociceptive activity for a period measured in hours, i.e. for at least 1 hour, without significant entry into the brain.

Although the preferred amino acid sequences are set forth in the foregoing formulas, it should be understood by those having ordinary skill in the peptide chemistry art that one or more of the recited amino acid residues might be substituted by a conservative amino acid substitution, e.g. one basic amino acid for another, or one hydrophobic amino acid for another, e.g. D-Ile for D-Leu. Likewise, various of the residues may also be modified as generally known in this art; for example, D-Phe (as earlier indicated) may be modified by incorporating a halogen or nitro group usually at the 3- or 4-position, or both, or the alpha-carbon may be methylated. Such modifications are considered to produce equivalent kappa receptor opioid peptides.

The peptides can be synthesized by any suitable method, such as by exclusively solid phase techniques or classical solution addition or alternatively by partial solid phase techniques or by fragment condensation techniques. For example, the techniques of exclusively solid-phase peptide synthesis (SPPS) are set forth in the textbook Stewart & Young, *Solid-Phase Peptide Synthesis,* 2nd Ed., Pierce Chemical Company, Rockford, Ill., 1984, and are exemplified by the disclosure of U.S. Pat. No. 4,105,603. The fragment condensation method of synthesis is exemplified in U.S. Pat. No. 3,972,859, and other available syntheses are exemplified by U.S. Pat. Nos. 3,842,067 and 3,862,925. Classical solution addition synthesis is described in detail in Bodanzky et al., *Peptide Synthesis,* 2nd Ed., John Wiley & Sons, New York, 1976.

Common to coupling-type chemical synthesis of peptides is the protection of any labile side chain of an amino acid being coupled, and usually the protection also of the α-amino group, so that the addition takes place at the carboxyl group of the individual amino acid or dipeptide or tripeptide that is being added. Such protecting groups are well known in the art, and tert-butyloxycarbonyl (Boc), benzyloxycarbonyl(Z) and 9-fluorenylmethoxycarbonyl (Fmoc) are often used as preferred α-amino protecting groups in SPPS or classical solution synthesis although there are a large variety of other α-amino protecting groups that may alternatively be used.

When SPPS is used, the C-terminal amino-acid residue is coupled to a solid resin support such as O—$CH_2$-polystyrene support, O—$CH_2$-benzyl-polyamide resin support, —NH-benzhydrylamine (BHA) resin support, or —NH-para methylbenzhydrylamine (MBHA) resin support. The use of BHA or MBHA resins is often preferred when the unsubstituted amide is desired because cleavage directly gives the C-terminal amide. When an N-methylamide is desired, such can be generated from an N-methyl BHA resin. Other single-substituted amides can be synthesized by the procedure set forth in W. Kornreich et al., *Int. J. Peptide Protein Res.*, 25:414–420, 1985, and also in U.S. Pat. No. 4,701,499. Peptides having di-substituted amides at the C-terminus, such as N-morpholinyl or N-piperidinyl, are preferably prepared via classical solution synthesis or by fragment condensation in solution.

Once synthesized, these tetrapeptides are readily purified using well known state of the art methods for short peptide purification, for example, reverse-phase high performance liquid chromatography (RP-HPLC), or other appropriate methods. Such purification is described in detail in J. Rivier et al., *J. Chromatography*, 288:303–328, 1984, and C. Miller and J. Rivier, *Peptide Science, Biopolymers*, 40:265–317 (1996), and specific examples of such purification following solid phase synthesis or the like are shown in U.S. Pat. No. 5,098,995.

A variety of assays may be employed to test whether the tetrapeptides exhibit high selectivity for the KOR, strong antinociceptive bioactivity, long duration of in vivo bioactivity and lack of brain penetration. Receptor assays are well known in the art, and the mouse, rat, guinea-pig and human KORs have recently been cloned. With the exception of the gpKOR, the cloned KORs are very similar, all containing about 380 amino acids. The amino acid sequence of the hKOR has 93.9% and 93.4% homology with the rKOR and the mKOR, respectively. By contrast, the hKOR differs significantly from the hMOR and from the human delta opioid receptor (hDOR), having respectively only 60.2% and 59.1% amino acid sequence identity. KORs as well as other opioid receptors are classical, seven-transmembrane spanning, G-protein coupled receptors (Gi). These cloned receptors readily allow a particular candidate peptide to be screened; for example, screening against both KOR and MOR may be carried out in order to determine the selectivity. The human KOR, MOR and DOR have been stably expressed in a mouse cancer cell line derived from a hippocampal neuroblastoma (HN.9.10) and are available for use in in vitro screening. There are also a number of well-accepted in vivo tests that have generally become standards for determining the antinociceptive activity of an opioid compound. These tests generally employ mice and include the tail flick test, the paw-pressure test, the acetic acid writhing test, the tail-pinch test and the tail-immersion test. Vonvoigtlander, P. F. et al., *J. Pharm. Exper. Therapeutics*, 224:7–12 (1983) describes a number of such tests for opioid compounds.

Binding affinity refers to the strength of interaction between ligand and receptor. To demonstrate binding affinity for opioid receptors, the peptides of the invention were evaluated using competition binding studies. These studies were performed using cloned human kappa (hKOR) and mu opioid (hMOR) receptors expressed in stable transfected cell lines (HN9.10, derived from a mouse hippocampal neuroblastoma). In these studies, the test compounds (unlabeled or cold ligand) are used at increasing concentrations to displace the specific binding of a radiolabeled ligand that has high affinity and selectivity for the receptor studied. $^3$H-U-69,593 and $^3$H-DAMGO were used as ligands in hKOR and hMOR studies, respectively. Both ligands are commercially available (NEN-Dupont). DAMGO is an acronym for [D-Ala$^2$, MePhe$^4$, Gly-ol$^5$]-enkephalin. The affinity of the radioligands is defined by the concentration of radioligand that results in half-maximal specific binding ($K_D$) in saturation studies. The $K_D$ for $^3$H-U-69,593 at hKOR and for $^3$H-DAMGO at hMOR are about 0.3 nM and 3.0 nM, respectively. The affinity of the test compound (unlabeled or cold ligand) is determined in competition binding studies by calculating the inhibitory constant ($K_i$) according to the following formula:

$$K_i = \frac{IC_{50}}{1 + (F/K_D)}$$

where

IC$_{50}$=Concentration of the cold ligand that inhibits 50% of the specific binding of the radioligand F=Free radioligand concentration $K_D$=Affinity of the radioligand determined in saturation studies.

When performing these assays under specific conditions with relatively low concentrations of receptor, the calculated $K_i$ for the test compound is a good approximation of its dissociation constant $K_D$, which represents the concentration of ligand necessary to occupy one-half (50%) of the binding sites. A low $K_i$ value in the nanomolar and subnanomolar range is considered to identify a high affinity ligand in the opioid field. Preferred analogs have a $K_i$ for KOR of about 2 nanomolar (nM) or less, whereas more preferred analogs have a $K_i$ of about 1 nM or less. Because KOR receptors are distributed widely throughout the body, kappa receptor opioid peptides will have a substantial effect in modulating many peripheral actions, and if they are highly KOR-selective, they will have minimal side-effects and should be good drugs physiologically.

These binding assays employing KORs and MORs are straightforward to perform and can be readily carried out with initially identified or synthesized peptides to determine whether such peptides are KOR-selective and have high affinity. Such binding assays can be carried out in a variety of ways as well known to one of skill in the art, and one detailed example of an assay of this general type is set forth in Perrin, M., et al., *Endocrinology*, 118:1171–1179, 1986.

The present invention is further described by the examples which follow. Such examples, however, are not to be construed as being limiting in any way to either the spirit or scope of the present invention which is described by the claims at the end hereof.

EXAMPLE 1

The peptide having the formula: H-D-Phe-D-Phe-D-Nle-D-Arg-NHEt is appropriately synthesized as well known in the peptide synthesis art. For example, the tripeptide: (α-amino protecting group)D-Phe-D-Phe-D-Nle(carboxyl protecting group), is initially synthesized using classical solution chemistry. For example, the tripeptide may be prepared by dissolving H-D-Nle-OMe in DMF and adding N-ethylmorpholine (NEM) or the like to adjust the pH. This solution is then combined with a solution of Boc-protected D-Phe-OH in DMF containing NEM. To this reaction mixture there is added an activating or coupling agent, such as benzotriazole-1-yl-oxy-tris-(dimethylamino)-phosphonium hexafluorophosphate (BOP) or a mixture of N,N'-diisopropylcarbodiimide (DIC) and N-hydroxybenzotriazole (HOBt). Following completion of the reaction, the medium is evaporated to dryness, and the product is then appropriately purified and recrystallized. The Boc-protecting group is then removed with trifluoroacetic acid (TFA), and the dipeptide is redissolved in DMF. A solution of Boc-protected D-Phe dissolved in DMF, with NEM, is added. The reaction is repeated using BOP, as described above, to create the tripeptide which, after the solution is evaporated to dryness, is purified and recrystallized. The product which results is Boc-D-Phe-D-Phe-D-Nle-OCH$_3$. The methylester is then suitably converted to the free acid, as by dissolving in a mixture of dioxane or DMSO and water and adding sodium hydroxide. Following completion of the reaction, separation, purification and recrystallization provide the tripeptide Boc-D-Phe-D-Phe-D-Nle-OH.

The tripeptide is dissolved in DMF containing NEM, and reacted with D-Arg(Tos)-NHEt, again using BOP as a coupling agent. Alternatively, the tripeptide methyl ester may be converted to the azide, if desired, by treatment with an 80% solution of hydrazine hydrate to produce the hydrazide, which is isolated and then treated with sodium nitrite and mineral acid in DMF. The azide is immediately reacted with D-Arg(Tos)-NHEt in DMF solution containing triethylamine. Following completion of the reaction, the mixture is evaporated to dryness, then suitably purified and recrystallized. The N-terminus and the side chain of D-Arg are then deprotected, and purification and recrystallization are again carried out, producing the desired tetrapeptide ethylamide (Peptide No. 1).

The peptide is judged to be homogenous by reversed phase HPLC using two different mobile phases: a gradient of acetonitrile in water containing 0.1% trifluoroacetic acid and a gradient of acetonitrile in triethylamine phosphate buffer pH 7, and also by fused silica, capillary electrophoresis using a phosphate buffer of pH 2.5. The purity of the peptide by these methods is estimated to be >98%. Mass spectrometry using electrospray ionization and ion trap analysis showed a pseudomolecular ion [MH]$^+$ at m/z 609.4 which is consistent with the calculated mass of m/z 609.5 for this tetrapeptide. Fragmentation analysis of the pseudomolecular ion showed a series of ions at m/z ratios consistent with the sequence of amino acids expected for the prepared structure.

Binding assays with cells expressing human KOR and MOR are carried out as mentioned hereinbefore. The affinities of the test peptide for hKOR and hMOR, stably expressed in mouse hippocampal neuroblastoma (HN.9.10) cells, are determined by competitive displacement of $^3$H-U-69,593 for hKOR or of $^3$H-DAMGO for hMOR as described. Data from at least 3 experiments are pooled, and inhibitory dissociation constant (K$_i$) values (95% confidence limits) are calculated using a suitable program, such as the LIGAND program of Munson and Rodbard, *Anal. Biochem*, 107:220–239, 1980. The cloned KOR binds Peptide No. 1 with high affinity as determined by the competitive displacement of bound radioligand, and the K$_i$ is determined to be about 0.05±0.02 nM. The difference in affinity is dramatic compared to similar stably transfected cancer cells expressing human MOR where the K$_i$ is 1890±990 nM. Thus, Peptide No. 1 binds more strongly to hKOR than to hMOR by a factor of about 38,000.

Testing of the peptide in the mouse acetic acid writhing assay (as described hereinafter) shows an ED$_{50}$ of about 0.09 mg/kg and that the peptide continues to exhibit over 50% antinociception after 3 hours. Thus, Peptide No. 1 is considered to exhibit very long duration of action.

EXAMPLE 2

Opioid peptides having the general formula: H-D-Phe-D-Phe-D-Nle-D-Arg-Q, as indicated in TABLE A, are synthesized and tested as described in EXAMPLE 1.

TABLE A

| No | Q | K$_i$ KOR (nM) | K$_i$ MOR (nM) | μ/κ Ratio | Mass Spectroscopy Calculated | Mass Spectroscopy Measured | WT-ED$_{50}$ mg/kg |
|---|---|---|---|---|---|---|---|
| 2 | NHMe | 0.06 | 3,620 | 60,000 | 0 595.4 | 595.5 | 0.14 |
| 3 | NHPr | 0.09 | 1,640 | 18,000 | 623.4 | 623.5 | 0.078 |
| 4 | NHBu | 0.19 | 1,370 | 7,200 | 637.4 | 637.5 | 0.30 |
| 5 | NH(Cyp) | 0.18 | 3,520 | 20,000 | 621.4 | 621.5 | 0.04 |
| 6 | Mor | 0.06 | 2,510 | 42,000 | 651.4 | 651.4 | 0.014 |
| 7 | N(Et$_2$) | 0.11 | 1,900 | 17,000 | 637.4 | 637.5 | 0.02 |
| 8 | NH(4-Pic) | 0.14 | 3,640 | 26,000 | 672.4 | 672.4 | 0.01 |
| 9 | NHhEt | 0.40 | 1,010 | 2,500 | 625.4 | 625.5 | 0.03 |
| 10 | Tmo | 0.09 | 2,260 | 25,000 | 667.4 | 667.3 | 0.067 |
| 11 | 4-HyP | 0.06 | 3,700 | 62,000 | 665.4 | 665.4 | 0.073 |
| 12 | Pip | 0.15 | 1,050 | 7,000 | 649.4 | 649.5 | 0.07 |
| 13 | NH(2-Tzl) | 0.59 | 1,590 | 2,700 | 664.3 | 664.4 | 0.44 |
| 14 | NHBzl | 0.44 | 890 | 2,000 | 671.4 | 671.4 | 0.14 |
| 15 | Ppz | 0.16 | 9,100 | 57,000 | 650.4 | 650.5 | 0.017 |

Peptides 2 to 15 are considered to exhibit long duration of antinociceptive bioactivity.

EXAMPLE 3

Opioid peptides having the general formula: H-Xaa$_1$-Xaa$_2$-Xaa$_3$-Xaa$_4$-Q, as indicated in TABLE B, are synthesized and tested as described in EXAMPLE 1.

TABLE B

| No | Xaa$_1$ | Xaa$_2$ | Xaa$_3$ | Xaa$_4$ | Q |
|---|---|---|---|---|---|
| 16 | D-4Fpa | D-Phe | D-Nle | D-Arg | NHEt |
| 17 | D-Acp | D-Phe | D-Nle | D-Arg | NHEt |
| 18 | D-Ala(Thi) | D-Phe | D-Nle | D-Arg | NHEt |
| 19 | D-Tyr | D-Phe | D-Nle | D-Arg | Mor |
| 20 | D-Phe | D-Trp | D-Nle | D-Arg | Mor |
| 21 | D-Phe | D-4NO$_2$Phe | D-Nle | D-Arg | Mor |
| 22 | D-Phe | D-4Cpa | D-Nle | D-Arg | Mor |
| 23 | D-Phe | D-1Nal | D-Nle | D-Arg | NH(4Pic) |
| 24 | D-Phe | D-2Nal | D-Nle | D-Arg | NH(4Pic) |
| 25 | D-Phe | D-Tyr | D-Nle | D-Arg | NH(4Pic) |
| 26 | D-Phe | D-Phe | D-Leu | D-Arg | Mor |
| 27 | D-Phe | D-Phe | D-Val | D-Arg | Mor |
| 28 | D-Phe | D-Phe | D-Acp | D-Arg | Mor |
| 29 | D-Phe | D-Phe | D-Nle | D-Lya | Mor |
| 30 | D-Phe | D-Phe | D-Nle | D-Har | NHEt |
| 31 | D-Phe | D-Phe | D-Nle | D-Har(Et$_2$) | NHEt |
| 32 | D-Phe | D-Phe | D-Nle | D-Orn | NHEt |
| 33 | D-Phe | D-Phe | D-Nle | D-Amf | NH(4Pic) |
| 34 | D-Phe | D-Phe | D-Nle | D-Dbu | NH(4Pic) |
| 35 | D-Phe | D-Phe | D-Leu | D-Orn | NH(4Pic) |
| 36 | D-Phe | D-Phe | D-Phe | D-Arg | NH(4Pic) |
| 37 | D-Phe | D-Phe | D-Nle | D-Ily | NH(4Pic) |
| 38 | D-Phe | D-Phe | D-Nle | D-Ior | NH(4Pic) |
| 39 | D-Phe | D-4Mpa | D-Nle | D-nArg | Mor |

Peptides 16 to 39 are considered to exhibit long duration of antinociceptive bioactivity.

EXAMPLE 4

Opioid peptides having the general formula: H-Xaa$_1$--Xaa$_3$-Xaa$_2$-Xaa$_4$-Q, as indicated in TABLE C, are synthesized tested as described in EXAMPLE 1.

TABLE C

| No. | Xaa$_1$ | Xaa$_2$ | Xaa$_3$ | Xaa$_4$ | Q | Mass Spectroscopy Calculated | Mass Spectroscopy Measured | Binding (μ/k ratio) |
|---|---|---|---|---|---|---|---|---|
| 40 | D-Phe | D-Phe | D-Nle | D-Arg | NH-4Nhz | 716.4 | 716.5 | 3,800 |
| 41 | D-Phe | D-Phe | D-Nle | D-Arg | NH-4-Ahz | 686.4 | 686.4 | 12,000 |
| 42 | D-Phe | D-Phe | D-Nle | D-Arg | Ecp | 721.4 | 721.5 | 27,000 |
| 43 | D-CMP | D-Phe | D-Nle | D-Arg | NH(4Pic) | 686.4 | 686.5 | 2,500 |
| 44 | D-Phe | D-Phe | D-Acp | D-Arg | NH(4Pic) | 698.4 | 698.5 | 8,200 |
| 45 | D-Phe | D-Phe | D-Hle | D-Arg | NH(4Pic) | 686.4 | 686.5 | 11,000 |
| 46 | D-Phe | D-Phe | D-CML | D-Oro | Mor | 623.4 | 623.4 | 14,000 |
| 47 | D-Phe | D-Phe | D-Lcu | D-Lys | NH(4Pic) | 644.4 | 644.3 | 30,000 |
| 48 | D-Phe | D-Phe | D-Lcu | D-Lys | NHPr | 595.4 | 595.3 | 18,000 |
| 49 | D-Phe | D-Phe | D-Lcu | D-Lys | Mor | 623.4 | 623.3 | 92,000 |
| 50 | D-Phe | D-Phe | D-Nle | D-Har | NH(4Pic) | 686.4 | 686.5 | 9,300 |
| 51 | D-Phe | D-Phe | D-Nle | D-Har | Mor | 665.4 | 665.5 | 12,000 |
| 52 | D-Phe | D-Phe | D-Lcu | D-Dbu | NH(4Pic) | 616.4 | 616.3 | 92,000 |
| 53 | D-Phe | D-Phe | D-Lcu | D-Dbu | Mor | 595.4 | 595.3 | 85,000 |

Peptides 40 to 53 are considered to exhibit long duration of antinociceptive bioactivity.

EXAMPLE 5

Opioid peptides having the general formula: H-D-Phe-Xaa$_2$-Xaa$_3$-Xaa$_4$-Q, as indicated in TABLE D, are synthesized tested as described in EXAMPLE 1.

TABLE D

| No | Xaa$_2$ | Xaa$_3$ | Xaa$_4$ | Q | K$_i$ KOR (nM) | K$_i$ MOR (nM) | μ/κ Ratio | Mass Spectroscopy Calculated | Mass Spectroscopy Measured | WT-ED$_{50}$ mg/kg |
|---|---|---|---|---|---|---|---|---|---|---|
| 54 | D-Phe | D-Nle | D-Arg | NH(3Pic) | 0.39 | 1,220 | 3,100 | 672.4 | 672.5 | |
| 55 | D-Phe | D-Nle | D-Amf | NHEt | 0.14 | 1,750 | 12,500 | 629.4 | 629.3 | |
| 56 | D-Phe | D-Leu | D-Orn | NHEt | 0.31 | 4,150 | 13,000 | 567.4 | 567.4 | 0.057 |
| 57 | D-Phe | D-Leu | D-Onn | Mor | 0.19 | 5,260 | 28,000 | 609.4 | 609.3 | 0.026 |
| 58 | D-Phe | D-Nle | D-Gmf | Mor | 0.46 | 3,010 | 6,500 | 713.4 | 713.5 | 0.040 |

Peptides 54 to 58 are considered to exhibit long duration of antinociceptive bioactivity.

EXAMPLE 6

Opioid peptides having the general formula: H-Xaa$_1$-Xaa$_2$-D-Leu-D-Arg-Q, as indicated in TABLE E, are synthesized and tested as described in EXAMPLE 1.

TABLE E

| No | Xaa$_1$ | Xaa$_2$ | Q | K$_i$ KOR (nM) | K$_i$ MOR (nM) | μ/κ Ratio | Mass Spectroscopy Calculated | Mass Spectroscopy Measured | WT-ED$_{50}$ mg/kg |
|---|---|---|---|---|---|---|---|---|---|
| 59 | D-Ala(2Thi) | D-4Cpa | Mor | 0.25 | 3,360 | 13,000 | 691.3 | 691.1 | 0.052 |
| 60 | D-Ala(2Thi) | D-3,4Cpa | NH(4Pic) | 0.4 | 769 | 1,900 | 746.3 | 746.3 | 0.083 |
| 61 | D-Ala(2Thi) | D-3,4Cpa | Mor | 0.15 | 1,560 | 10,400 | 725.3 | 725.4 | |
| 62 | D-4Fpa | D-2Nal | Mor | 0.33 | 1,145 | 3,500 | 719.4 | 719.5 | |
| 63 | D-Ala(2Thi) | D-2Nal | Mor | 0.2 | 3,170 | 16,000 | 707.4 | 707.4 | 0.04 |
| 64 | D-Ala(2Thi) | D-4Cpa | NH(4Pic) | 0.31 | 2,375 | 7,700 | 712.3 | 712.4 | 0.076 |
| 65 | D-4Fpa | D-4Cpa | Mor | 0.17 | 1,900 | 11,000 | 703.4 | 703.4 | 0.15 |

Peptides 59 to 65 are considered to exhibit long duration of antinociceptive bioactivity.

EXAMPLE 7

Opioid peptides having the general formula: H-Xaa$_1$-Xaa$_2$-Xaa$_3$-Xaa$_4$-Q, as indicated in TABLE F, are synthesized and tested as described in EXAMPLE 1.

TABLE F

| No | Xaa$_1$ | Xaa$_2$ | Xaa$_3$ | Xaa$_4$ | Q |
|---|---|---|---|---|---|
| 66 | D-4Cpa | D-4Cpa | D-Leu | D-Lys | NHPr |
| 67 | D-4Fpa | D-2Nal | D-Met | D-Amf | NHBu |

TABLE F-continued

| No | Xaa$_1$ | Xaa$_2$ | Xaa$_3$ | Xaa$_4$ | Q |
|---|---|---|---|---|---|
| 68 | D-4Cpa | D-Trp | D-Acp | D-Amf | Pip |
| 69 | D-Phe | D-Phe | D-Val | D-Orn | 4-Ecp |
| 70 | D-Ala(2Thi) | D-4Fpa | D-Nle | D-Dbu | NH4Abz |
| 71 | D-Acp | D-Phe | D-Leu | D-Har | 4HyP |
| 72 | D-CMP | D-Trp | D-Phe | D-Arg(Et$_2$) | NHBzl |
| 73 | D-4Cpa | D-3,4Cpa | D-Met | D-Orn | Tmo |
| 74 | D-Acp | D-1Nal | D-Nle | D-Har(Et$_2$) | NH(3Pic) |
| 75 | D-4Fpa | D-4Cpa | D-Leu | D-Amf(Amd) | NHhEt |
| 76 | D-CMP | D-Tyr | D-Acp | D-Dbu | NHIpr |
| 77 | D-Phe | D-2Nal | D-Acp | D-Ily | NHPn |
| 78 | D-Tic | D-4Fpa | D-Phe | D-Lys | NH(4Pic) |
| 79 | D-4NO$_2$Phe | D-Trp | D-CML | D-CML | N(Et)$_2$ |
| 80 | D-CMP | D-Phe | D-Met | D-Ior | Mor |
| 81 | D-Ala(3Thi) | D-1Nal | D-Nle | D-Lys | NH(2-Tzl) |
| 82 | D-Phe | D-4NO$_2$Phe | D-Nle | D-Arg | NHCyp |
| 83 | D-Acp | D-2Nal | D-Hle | D-Har | NHCyb |
| 84 | D-Tyr | D-2Nal | D-Phe | D-Lys | Ppz |
| 85 | D-Phe | D-1Nal | D-Met | D-Ior | OxP |
| 86 | D-Phe | D-Trp | D-Met | D-Arg | Dmp |
| 87 | D-Phe | D-Trp | D-Nle | D-Orn | Mor |

The opioid peptides of Table F are considered to show high selectivity for the KOR, as compared to the MOR, and to exhibit antinociceptive bioactivity in vivo.

EXAMPLE 8

Opioid peptides having the general formula: H-Xaa$_1$-Xaa$_2$-Xaa$_3$-Xaa$_4$-Q, as indicated in TABLE G, are synthesized and tested as described in EXAMPLE 1.

TABLE G

| No | Xaa$_1$ | Xaa$_2$ | Xaa$_3$ | Xaa$_4$ | Q | μ/k ratio |
|---|---|---|---|---|---|---|
| 88 | D-4Fpa | D-Phe | D-Nle | D-Arg | NH(4Pic) | 16,000 |
| 89 | D-3Fpa | D-Phe | D-Nle | D-Arg | NH(4Pic) | 24,000 |
| 90 | D-2Fpa | D-Phe | D-Nle | D-Arg | NH(4Pic) | 38,000 |
| 91 | D-4Fpa | D-Phe | D-Nle | D-Har | NH(4Pic) | |
| 92 | D-4Cpa | D-Phe | D-Nle | D-Arg | NH(4Pic) | 2,900 |
| 93 | D-4Fpa | D-4Npa | D-Nle | D-Arg | NH(4Pic) | 1,200 |
| 94 | D-Phe | D-Phe | D-Leu | D-Orn | Dor | 85,000 |
| 95 | D-Phe | D-Phe | D-Nle | D-nArg | NH(4Pic) | 16,000 |
| 96 | D-Phe | D-Phe | D-Leu | D-CMO | NH(4Pic) | |
| 97 | D-Phe | D-Phe | D-Nle | D-Arg | NH-Ahx | |
| 98 | D-Phe | D-Phe | D-Leu | D-Orn | NH-Aeb | 24,000 |

Peptides 88 to 98 are considered to exhibit long duration of antinociceptive bioactivity.

EXAMPLE 9

Selected peptides that are identified in Tables A–G have been further specifically subjected to in vivo testing for determination of duration of action of their opioid properties, and the results are reported in Table H hereinafter. The peptide numbers correspond to those in the earlier tables and the figures with regard to μ/K ratio are simply carried over for reference purposes. The in vivo testing is carried out using a mouse writhing test (WT) that is well-suited for determining the length of duration of antinociceptive biological activity. This test is described in detail in an article by G. A. Bentley et al., *Br. J. Phamac.*, 73:325–332, 1981, and it employs conscious male ICR mice which are purchased from Harlan and which weigh between 20 and 30 grams. The mice are fasted for 12 to 16 hours prior to beginning the test. The nociceptive behavior, i.e. writhing, to be monitored is induced by the intraperitoneal (i.p.) administration of dilute acetic acid. 10 milliliters of 0.6% aqueous acetic acid is used per kg of body weight. Writhing is scored during the 15 minutes following acetic acid administration. In a first step, compounds are tested at 3 to 4 increasing doses, given by intravenous route, and at one unique pretreatment time (–5 minutes before acetic acid injection). This step is used to determine the potency (WT-ED$_{50}$) as well as a submaximal effective dose (about 80–90% antinociception). In a second step, this submaximal effective dose for each specific peptide is administered at various pretreatment times (i.e. –5 minutes, –60 minutes, –120 minutes and –180 minutes) prior to the administration of the acetic acid in order to determine the duration of action. Throughout the test, a control group of mice are used which are administered only the vehicle without the candidate peptide. The number of writhes are counted over a 15-minute period, starting from the time of acetic acid injection, and bioactivity, i.e. antinociception, is expressed as a percentage, and is calculated as follows:

100×(writhes in control group–writhes in treated group)/writhes in control group Because each submaximal dose will very likely vary so as not to be directly comparable, the results are normalized mathematically, as known in this art, to provide comparable values which are set forth in Table H. In Table H, the antinociceptive activity remaining after 1, 2, and 3 h is expressed as percentage of the activity found at –5 min. Values higher than 100% indicate greater antinociception than at the beginning of the experiment. It is felt that the opioid peptide should be effective to reduce writhing by at least about 25% at a time of 1 hour to be considered to have long duration of in vivo action.

In addition to using this test to determine duration of antinociceptive activity, it is also used to measure the in vivo biopotency (short term) of the peptide. This value is given in the table under the heading WT-ED$_{50}$ in milligrams per kg of body weight. The value is a measure of the dosage necessary to reduce the number of writhes in the mouse being tested by 50% (as compared to a control mouse) over a period of 15 minutes.

TABLE H

| Peptide No. | μ/κ Ratio | WT-ED$_{50}$ mg/kg | % Antinociception | | |
|---|---|---|---|---|---|
| | | | 1 hr | 2 hr | 3 hr |
| 1 | 38,000 | 0.09 | 83.9 | 75.5 | 61.3 |
| 2 | 60,000 | 0.14 | 70.5 | 29.8 | |
| 3 | 18,000 | 0.078 | 29 | 30.7 | |
| 4 | 7,200 | 0.3 | 49.3 | | |
| 5 | 20,000 | 0.04 | 66 | 34.5 | |
| 6 | 42,000 | 0.014 | 105.7 | 52.7 | |
| 7 | 17,000 | 0.02 | 67.5 | 36.8 | |
| 8 | 26,000 | 0.01 | 66.9 | 45.1 | |
| 9 | 2,500 | 0.03 | 72.5 | 39.5 | |
| 10 | 25,000 | 0.07 | 81.6 | 47.5 | |
| 11 | 62,000 | 0.07 | 61.8 | 36.9 | |
| 12 | 7,000 | 0.07 | 60.5 | 53.6 | |
| 13 | 2,700 | 0.44 | 30.7 | | |
| 14 | 2,000 | 0.14 | 36 | | |
| 42 | 27,000 | 0.06 | 45.3 | 29.4 | |
| 56 | 13,000 | 0.06 | 76.3 | 60.2 | |
| 57 | 28,000 | 0.026 | 100 | 67.2 | 58.2 |

TABLE H-continued

| Peptide No. | μ/κ Ratio | WT-ED$_{50}$ mg/kg | % Antinociception 1 hr | 2 hr | 3 hr |
|---|---|---|---|---|---|
| 59 | 13,000 | 0.052 | 83.3 | 59.7 | |
| 60 | 1,900 | 0.083 | 83.8 | 35.5 | |
| 63 | 16,000 | 0.04 | 51.8 | 36.1 | |
| 65 | 11,000 | 0.031 | 39.5 | | |

The opioid peptides are useful as analgesics and for other pharmacological applications to treat pathologies associated with the KOR system. They exhibit advantages over μ agonist painkillers, e.g. morphine which has undesirable effects, such as constipation, respiratory depression and itching. It is highly desirable that these opioid peptides do not significantly cross the blood/brain barrier, to safeguard against potential side effects that may result. The safety of these compounds with regard to brain penetration is assessed by comparison of their potency to elicit peripheral effects versus their potency to elicit central effects. Peripheral effects are measured using the mouse writhing test (WT) described previously. Central effects due to action on kappa receptors located in the brain are measured using the mouse tail-flick test (TF).

The tail-flick test is an assay of acute somatic pain, designed to evaluate the potency and duration of action of centrally acting analgesics. Nociception induced by tail-dip into hot water (52° C.) results in a rapid tail withdrawal, also known as tail-flick. Centrally acting analgesic compounds are expected to increase in a dose-related manner the latency for tail withdrawal. The test is described in Vanderah, T. W. et al., *J. Pharm. Exper. Therapeutics,* 262:190–197, 1992.

Safety is evaluated through the use of a Brain Penetration Index (BPI), which is defined as:

$$BPI = \frac{TF - ED_{50}}{WT - ED_{50}}$$

where the ED$_{50}$ values are the doses that produce half maximal effect in the mouse writhing test (WT-ED$_{50}$) and the mouse tail-flick test (TF-ED$_{50}$), respectively, when given by i.v. route. A high BPI value signals low brain penetration and indicates that the compound is likely to exhibit a wide margin of safety (lack of brain side effects) when used for the purposes described in this application. The preferred opioid peptides have BPI values equal to or higher than 100, with more preferred opioid peptides having a BPI higher than 300. Systemic nonpeptidic kappa agonists (e.g. Enadoline and U-69,593) have BPI values lower than 5, which indicates significant brain penetration is occurring as also evidenced by the side effects (diuresis, dysphoria, and sedation) they produce when used clinically. BPI values for some representative opioid peptides are shown in Table I which follows:

TABLE I

| Peptide No. | WT-ED$_{50}$ mg/kg | TF-ED$_{50}$ mg/kg | BPI |
|---|---|---|---|
| 1 | 0.09 | 9.7 | 108 |
| 3 | 0.078 | 13.82 | 177 |
| 5 | 0.04 | 4.4 | 110 |
| 6 | 0.014 | 6.4 | 457 |
| 7 | 0.020 | 3.1 | 155 |
| 8 | 0.01 | 9.84 | 984 |
| 57 | 0.026 | 5.6 | 215 |

Because these peptides bind strongly to the KOR, they are also useful in in vitro assays for studying receptors and for determining what receptors may be present in a particular tissue sample. Thus, they are useful for diagnosis in this respect and potentially also for in vivo diagnosis.

Generally, these opioid peptides can be used to achieve antinociception in treating visceral pain and also to treat rheumatoid arthritis. They are particularly useful in treating abdominal postsurgery symptoms such as digestive disorders and pain. They are also considered to be effective to treat IBS, bladder instability, incontinence, and other indications where local inflammation results in pain states in the gut or in other viscera, e.g. inflammatory bowel disease (IBD) and dysmennorhea. The opioid peptide's ability to lower immune response might be advantageous in combating IBD and other indications, such as autoimmune diseases. Administration of the peptides can be employed to produce local analgesic activity in respect of both acute and chronic inflammatory conditions. They can be used to treat digestive ileus having symptoms such as bloating, nausea or intestinal transit inhibitions associated with pain, e.g. bowel obstruction possibly caused by spastic contractions. The opioid peptides are also effective in producing peripheral analgesia, and they can be targeted to relieve post-operative pain, as well as chronic pain, such as that caused by inflammation of gastrointestinal and visceral tissues, and also to give relief during withdrawal from drug addiction.

The compounds of the invention may be administered in the form of pharmaceutically acceptable, nontoxic salts, such as acid addition salts, as well known in this art. Illustrative of such acid addition salts are hydrochloride, hydrobromide, sulphate, phosphate, nitrate, oxalate, fumarate, gluconate, tannate, pamoate, maleate, acetate, citrate, benzoate, succinate, alginate, malate, ascorbate, tartrate and the like. If the active ingredient is to be administered in tablet form, the tablet may contain a pharmaceutically-acceptable, nontoxic diluent which includes a binder, such as tragacanth, corn starch or gelatin. Intravenous administration in isotonic saline, phosphate buffer, mannitol or glucose solutions may also be effected.

The pharmaceutical compositions will usually contain an effective amount of the peptide in conjunction with a conventional, pharmaceutically-acceptable carrier or diluent. Generally, the composition will contain an antinociceptive amount, i.e. an amount which is effective to block pain. Usually, the dosage will be from about 1 microgram to about 10 milligrams of the peptide per kilogram of the body weight of the host when given intravenously. The compositions may be administered as needed; for example, they may be administered repeatedly at 3–6 hour intervals. The nature of these compounds may possibly permit effective oral administration; however, oral dosages might be higher. If desirable to deliver the opioid peptide over prolonged periods of time, for example, for periods of one week or more from a single administration, slow release, depot or implant dosage forms may be utilized. For example, a suitable, slow-release depot formulation for injection may contain the peptide or a salt thereof dispersed or encapsulated in a slow-degrading, nontoxic or non-antigenic polymer, such as a polylactic acid/polyglycolic acid polymer, as described in U.S. Pat. No. 3,773,919. It is also known that administration by slow-release can be accomplished via a silastic implant.

These compounds can be administered to mammals intravenously, subcutaneously, intramuscularly, percutaneously, intranasally, intrapulmonarily, intrarectally or intravaginally, to achieve antinociception, such as to reverse gastrointestinal transit inhibition induced by peritoneal irritation. They may be so used for alleviation of post-operative pain. Effective dosages will vary with the form of administration and the particular species of mammal being treated. An example of one typical dosage form is a bacteriostatic water solution at a pH of about 3 to 8, e.g. about 6, containing the peptide, which solution is continuously administered parenterally to provide a dose in the range of about 0.3 μg to 3 mg/kg of body weight per day. These compounds are considered to be well-tolerated in vivo, and they are considered to be particularly well-suited for administration by subcutaneous injection in a bacteriostatic water solution or the like.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. Other substituted D-Phe residues, such as (4Br)D-Phe or (2,4Cl$_2$)D-Phe, can be used in the 2-position. Both D-Lys(Bu) and D-Lys(Et$_2$) are considered to be equivalents of D-Ily and D-Arg(Et$_2$). The N-terminus of the tetrapeptide may be permethylated, as known in this art, if desired.

The disclosures of all U.S. patents hereinbefore mentioned are incorporated herein by reference. Particular features of the invention are emphasized in the claims which follow.

What is claimed is:

1. A synthetic opioid peptide amide having an affinity for the kappa opioid receptor which is at least 1,000 times its affinity for the mu opioid receptor and which exhibits long duration of action when administered in vivo, which peptide has the formula:

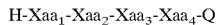

wherein Xaa$_1$ is (A)D-Phe, (C$^\alpha$Me)D-Phe, D-Tyr, D-Tic or D-Ala(cyclopentyl or thienyl), with A being H, NO$_2$, F, Cl or CH$_3$; Xaa$_2$ is (A')D-Phe, D-1Nal, D-2Nal, D-Tyr or D-Trp, with A' being A or 3,4Cl$_2$; Xaa$_3$ is D-Nle, (B)D-Leu, D-Hle, D-Met, D-Val, D-Phe or D-Ala(cyclopentyl) with B being H or C$^\alpha$Me; Xaa$_4$ is D-Arg, D-Har, D-nArg, D-Lys, D-Lys(Ipr), D-Arg(Et$_2$), D-Har(Et$_2$), D-Amf(G), D-Dbu, (B)D-Orn or D-Orn(Ipr), with G being H or amidino; and Q is NR$_1$R$_2$, morpholinyl, thiomorpholinyl, (C)piperidinyl, piperazinyl, 4-mono- or 4,4-di-substituted piperazinyl or δ-ornithinyl, with R$_1$ being lower alkyl, substituted lower alkyl, benzyl, substituted benzyl, aminocyclohexyl, 2-thiazolyl, 2-picolyl, 3-picolyl or 4-picolyl, R$_2$ being H or lower alkyl; and C being H, 4-hydroxy or 4-oxo.

2. The synthetic peptide according to claim 1 wherein Xaa$_2$ is D-Phe, Xaa$_3$ is D-Nle and Xaa$_4$ is D-Arg.

3. The synthetic peptide according to claim 1 wherein Q is NHR$_1$ and R$_1$ is ethyl, propyl, butyl, cyclopropyl or cyclobutyl.

4. The synthetic peptide according to claim 1 wherein Q is morpholinyl or thiomorpholinyl.

5. The synthetic peptide according to claim 1 wherein Q is NHR$_1$ and R$_1$ is 4-picolyl.

6. The synthetic peptide according to claim 1 wherein Xaa$_1$ is D-Ala(2-thienyl).

7. The synthetic peptide according to claim 1 wherein Xaa$_3$ is D-Nle or D-Leu and Xaa$_4$ is D-Orn or D-Amf(Amd).

8. The synthetic peptide according to claim 1 wherein Xaa$_2$ is D-Phe, Xaa$_3$ is D-Leu or D-CML and Xaa$_4$ is D-Orn.

9. The synthetic peptide according to claim 1 wherein Xaa$_1$ is D-4FPhe and Xaa$_2$ is D-4ClPhe.

10. A pharmaceutical composition which comprises an antinociceptive amount of a synthetic peptide according to claim 1 and a pharmaceutically acceptable liquid or solid carrier therefor.

11. A method of treatment which comprises administering an amount of the pharmaceutical composition of claim 10 which is effective (a) to achieve antinociception where there is visceral pain, rheumatoid arthritis, abdominal postsurgery symptoms or acute or chronic pain, or (b) to counteract bladder instability, incontinence or digestive ileus, or (c) to combat IBD or autoimmune diseases.

12. A synthetic opioid peptide amide having an affinity for the kappa opioid receptor which is at least 1,000 times its affinity for the mu opioid receptor, and an WT-ED$_{50}$ of about 0.5 mg/kg or less, and which exhibits long duration of action when administered in vivo, which peptide has the formula:

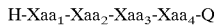

wherein Xaa$_1$ is D-Phe (unsubstituted or substituted by C$^\alpha$Me, 2F, 4F or 4Cl) or D-Ala(cyclopentyl or thienyl); Xaa$_2$ is (A')D-Phe, D-1Nal, D-2Nal or D-Trp, with A' being H, 4F, 4Cl, 4NO$_2$ or 3,4Cl$_2$; Xaa$_3$ is D-Nle, D-Leu, D-CML, D-Met or D-Acp; Xaa$_4$ is D-Arg, D-Arg(Et$_2$), D-Lys, D-Ily, D-Har, D-Har(Et$_2$), D-nArg, D-Orn, D-Ior, D-Dbu, D-Amf, and D-Amf(Amd); and Q is NR$_1$R$_2$, Mor, Tmo, Pip, 4-Hyp, OxP or Ppz, with R$_1$ being Me, Et, Pr, Bu, hEt, Cyp, Bzl or 4-picolyl, and R$_2$ being H or Et.

13. The synthetic peptide according to claim 12 wherein Xaa$_2$ is D-Phe, Xaa$_3$ is D-Nle and Xaa$_4$ is D-Arg.

14. The synthetic peptide according to claim 13 wherein Q is NHR$_1$ and R$_1$ is Et, hEt, Pr or 4-picolyl.

15. The synthetic peptide according to claim 12 wherein Q is NR$_1$R$_2$ and R$_1$ is ethyl and R$_2$ is ethyl.

16. The synthetic peptide according to claim 12 wherein Q is morpholinyl or thiomorpholinyl.

17. The synthetic peptide according to claim 12 wherein Q is NHR$_1$ and R$_1$ is ethyl or 4-picolyl.

18. The synthetic peptide according to claim 12 wherein Xaa$_1$ is D-Phe or D-Ala(2-thienyl) and Xaa$_2$ is D-4ClPhe.

19. The synthetic peptide according to claim 18 wherein Xaa$_3$ is D-Nle or D-Leu and Q is morpholinyl.

20. The synthetic peptide according to claim 12 having one of the following formulas:

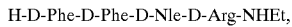

H-D-Phe-D-Phe-D-Nle-D-Arg-NH-4-picolyl,

H-D-Phe-D-Phe-D-Nle-D-Arg-NHPr,

H-D-Phe-D-Phe-D-Nle-D-Arg-thiomorpholinyl,

H-D-Phe-D-Phe-D-Nle-D-Arg-NEt$_2$,

H-D-Phe-D-Phe-D-Nle-D-Arg-NHMe,

H-D-Phe-D-Phe-D-Leu-D-Orn-morpholinyl,

H-D-Phe-D-Phe-D-Nle-D-Arg-NHhEt,

H-D-Phe-D-Phe-D-Nle-D-Arg-NH-cyclopropyl,

H-D-Ala(2Thi)-D-4Cpa-D-Leu-D-Arg-morpholinyl,

H-D-Phe-D-Phe-D-Nle-D-Arg-piperidinyl,

H-D-Phe-D-Phe-D-Leu-D-Orn-NHEt,

H-D-Phe-D-Phe-D-Leu-D-Lys-morpholinyl, and

H-D-Phe-D-Phe-D-Nle-D-Arg-piperazinyl.

21. A synthetic opioid peptide amide having an affinity for the kappa opioid receptor which is at least 1,000 times its affinity for the mu opioid receptor and an $ED_{50}$ of about 0.5 mg/kg or less, and which exhibits long duration of action when administered in vivo, which peptide has the formula:

H-Xaa$_1$-Xaa$_2$-Xaa$_3$-Xaa$_4$-Q wherein Xaa$_1$ is D-Phe, D-4Fpa, D-2Fpa, D-Acp or D-Ala(2Thi); Xaa$_2$ is (A)D-Phe, D-1Nal, D-2Nal or D-Trp, with A being 4F or 4Cl; Xaa$_3$ is D-Nle, D-Met or D-Leu; Xaa$_4$ is D-Arg, D-Har, D-nArg, D-Lys, D-Orn or D-Amf(Amd); and Q is NHR$_1$, Mor, Tmo, Pip or Ppz, with R$_1$ being Et, Pr or 4Pic.

* * * * *

UNITED STATES PATENT AND TRADEMARK OFFICE
CERTIFICATE OF CORRECTION

PATENT NO : 5,965,701
DATED : October 12, 1999
INVENTOR(S): Junien et al.

It is certified that error appears in the above-identified patent and that said Letters Patent is hereby corrected as shown below:

Column 4, lines 58-62, the formula should appear as follows:

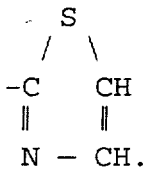

Signed and Sealed this

Twelfth Day of September, 2000

Attest:

Q. TODD DICKINSON

*Attesting Officer*          *Director of Patents and Trademarks*